United States Patent
Picano

(10) Patent No.: US 7,751,883 B2
(45) Date of Patent: Jul. 6, 2010

(54) SYSTEM AND METHOD FOR PROMOTING CORONARY ANGIOGENESIS

(75) Inventor: Eugenio Picano, Via Condotti 3/A, San Giuliano Terme (Pisa) (IT) 56010

(73) Assignee: Eugenio Picano, Pisa (IT)

( * ) Notice: Subject to any disclaimer, the term of this patent is extended or adjusted under 35 U.S.C. 154(b) by 909 days.

(21) Appl. No.: 11/380,048

(22) Filed: Apr. 25, 2006

(65) Prior Publication Data

US 2007/0249558 A1    Oct. 25, 2007

(51) Int. Cl.
    *A61N 1/362*    (2006.01)
(52) U.S. Cl. ............................... 607/9; 607/3
(58) Field of Classification Search .............. 607/1, 607/2, 3, 4, 5, 9, 14, 120, 122; 623/1.42
    See application file for complete search history.

(56) References Cited

U.S. PATENT DOCUMENTS

| | | | |
|---|---|---|---|
| 4,692,147 A | 9/1987 | Duggan | |
| 5,399,352 A * | 3/1995 | Hanson | 424/423 |
| 5,972,903 A * | 10/1999 | Barron et al. | 514/46 |
| 6,086,582 A * | 7/2000 | Altman et al. | 606/41 |
| 6,171,082 B1 | 1/2001 | Hankner et al. | |
| 6,199,554 B1 | 3/2001 | Mann et al. | |
| 6,206,914 B1 * | 3/2001 | Soykan et al. | 623/1.42 |
| 6,295,990 B1 * | 10/2001 | Lewis et al. | 128/898 |
| 6,416,510 B1 * | 7/2002 | Altman et al. | 606/41 |
| 6,463,323 B1 | 10/2002 | Contrad-Vlasak et al. | |
| 6,468,263 B1 * | 10/2002 | Fischell et al. | 604/890.1 |
| 6,547,787 B1 * | 4/2003 | Altman et al. | 606/41 |
| 6,671,558 B1 * | 12/2003 | Soykan et al. | 607/50 |
| 6,775,574 B1 | 8/2004 | Soykan et al. | |
| 7,072,711 B2 * | 7/2006 | Girouard et al. | 607/3 |
| 7,092,753 B2 * | 8/2006 | Darvish et al. | 604/21 |
| 2001/0044619 A1 * | 11/2001 | Altman | 604/539 |
| 2002/0010492 A1 | 1/2002 | Donovan et al. | |
| 2002/0183686 A1 * | 12/2002 | Darvish et al. | 604/21 |
| 2002/0188327 A1 * | 12/2002 | Struble | 607/9 |
| 2003/0083646 A1 * | 5/2003 | Sirhan et al. | 604/891.1 |
| 2004/0093034 A1 * | 5/2004 | Girouard et al. | 607/3 |
| 2004/0106953 A1 * | 6/2004 | Yomtov et al. | 607/3 |
| 2005/0113293 A1 * | 5/2005 | Larsen et al. | 514/9 |
| 2005/0149175 A1 * | 7/2005 | Hunter et al. | 623/1.42 |
| 2005/0154370 A1 | 7/2005 | Sigg et al. | |
| 2005/0209564 A1 * | 9/2005 | Bonner et al. | 604/173 |
| 2005/0238515 A1 | 10/2005 | Kent | |
| 2005/0249667 A1 * | 11/2005 | Tuszynski et al. | 424/9.3 |
| 2006/0030810 A1 | 2/2006 | Mandrusov et al. | |
| 2006/0041243 A1 * | 2/2006 | Nayak et al. | 604/506 |
| 2006/0041286 A1 | 2/2006 | Kanno et al. | |
| 2006/0147415 A1 * | 7/2006 | Mousa et al. | 424/78.37 |
| 2007/0275914 A1 * | 11/2007 | Manoharan et al. | 514/44 |

FOREIGN PATENT DOCUMENTS

WO    WO 9832859    7/1998

OTHER PUBLICATIONS

"Stress echo signals pacemaker risk", Am J. Med 2006; 118: 1381-1386, http://www.incirculation.net/arrhythmia//NewsItem/Stress-echo-signals-pacemaker-death-risk—Mar. 8, 2006.
Suzana Gligorova et al., "Pacing Stress Echocardiography", http://www.cardiovascularultrasound.com/content/3/1/36.

* cited by examiner

*Primary Examiner*—George R Evanisko
*Assistant Examiner*—Hiba El-Kaissi

(57) ABSTRACT

Systems and methods for promoting coronary angiogenesis employ a combination of mechanical, metabolic and biochemical stimuli.

9 Claims, 4 Drawing Sheets

SYSTEM AND METHOD FOR PROMOTING CORONARY ANGIOGENESIS

TECHNICAL FIELD

The present invention is related to cardiovascular therapy and more particularly to therapy promoting coronary angiogenesis.

BACKGROUND

It is estimated that five million people in the United States are afflicted with chronic stable angina resulting from ischemic episodes, many of which are caused by Coronary Artery Disease (CAD) in which one or more of the larger coronary arteries become obstructed or completely blocked by atherosclerotic plaque. Despite medical therapy and mechanical revascularization, for example, via angioplasty or bypass surgery, many patients suffering from CAD could benefit from additional protection against ischemia. One method of providing this additional protection is angiogenesis, or the development of new coronary vessels providing collateral circulation to myocardial tissue in proximity to obstructed arteries.

Experimental and clinical studies have demonstrated a protective role of collateral circulation in hearts having coronary obstructions. Unfortunately, the 'natural' process by which angiogenesis occurs may not be adequate to reverse ischemia in most CAD patients. But, there are several pieces of evidence indicating that it is possible to promote angiogenesis for the alleviation of myocardial ischemia. There are several conceptually and practically different approaches for angiogenic therapy.

A genetic approach, in which angiogenic growth factors, such as basic fibroblast growth factor, are administered (as proteins or as genes, with systemic or local direct myocardial delivery) is still under clinical investigation, has been shown to be of limited efficacy, and is burdened with the potential dangers of aberrant angiogenesis in non-targeted adjacent, or even remote, tissues, such as vulnerable atherosclerotic plaques, occult neoplasms, or diabetic retinopathy. Another approach involves the transfer of autologous stem cells to the ischemic region, producing a localized, effective angiogenetic response in the ischemic region.

A non-genetic approach to angiogenic therapy develops natural therapeutic strategies, potentiating them through physical and pharmacological stimuli. Three classes of stimuli have been proposed to promote coronary angiogenesis: exercise, adenosine-modulating drugs, and heparin. Each of these three, when used alone, do not seem to trigger clinically relevant angiogenesis that translates into improved exercise tolerance for CAD patients. Apparently, however, heparin and dipyridamole (an adenosine-modulating drug) critically potentiate exercise-induced angiogenesis and adenosine critically potentiates heparin-induced angiogenesis.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Constructions, materials, dimensions, and manufacturing processes suitable for making embodiments of the present are known to those of skill in the field of the invention.

Methods of the present invention combine mechanical, metabolic and biochemical stimuli to promote coronary angiogenesis. According to methods of the present invention, cardiac pacing is employed to provide the mechanical stimulus, which causes augmented coronary blood flow, comparable to that induced by exercise and accompanied by magnified endothelial shear stresses, and to evoke myocardial ischemia, which is the metabolic stimulus. When cardiac myocytes are rendered ischemic, collaterals may develop actively by growth with DNA replication and mitosis of endothelial and smooth muscle cells. Adenosine and heparin-binding growth factors, for example, Fibroblast Growth Factor, are among the mediators of this ischemia-induced angiogenesis. According to certain methods of the present invention, a period of pacing is 'sandwiched' between biochemical stimuli, which co-modulate, chaperone and amplify the metabolic stimulus, which is produced by the pacing-induced ischemia; the biochemical stimuli consist of exogenous heparin administered to potentiate heparin-binding growth factors, prior to pacing, and an adenosine-modulating drug, for example, dipyridamole, administered to potentiate the activity of endogenous adenosine, after pacing.

Figure 1:
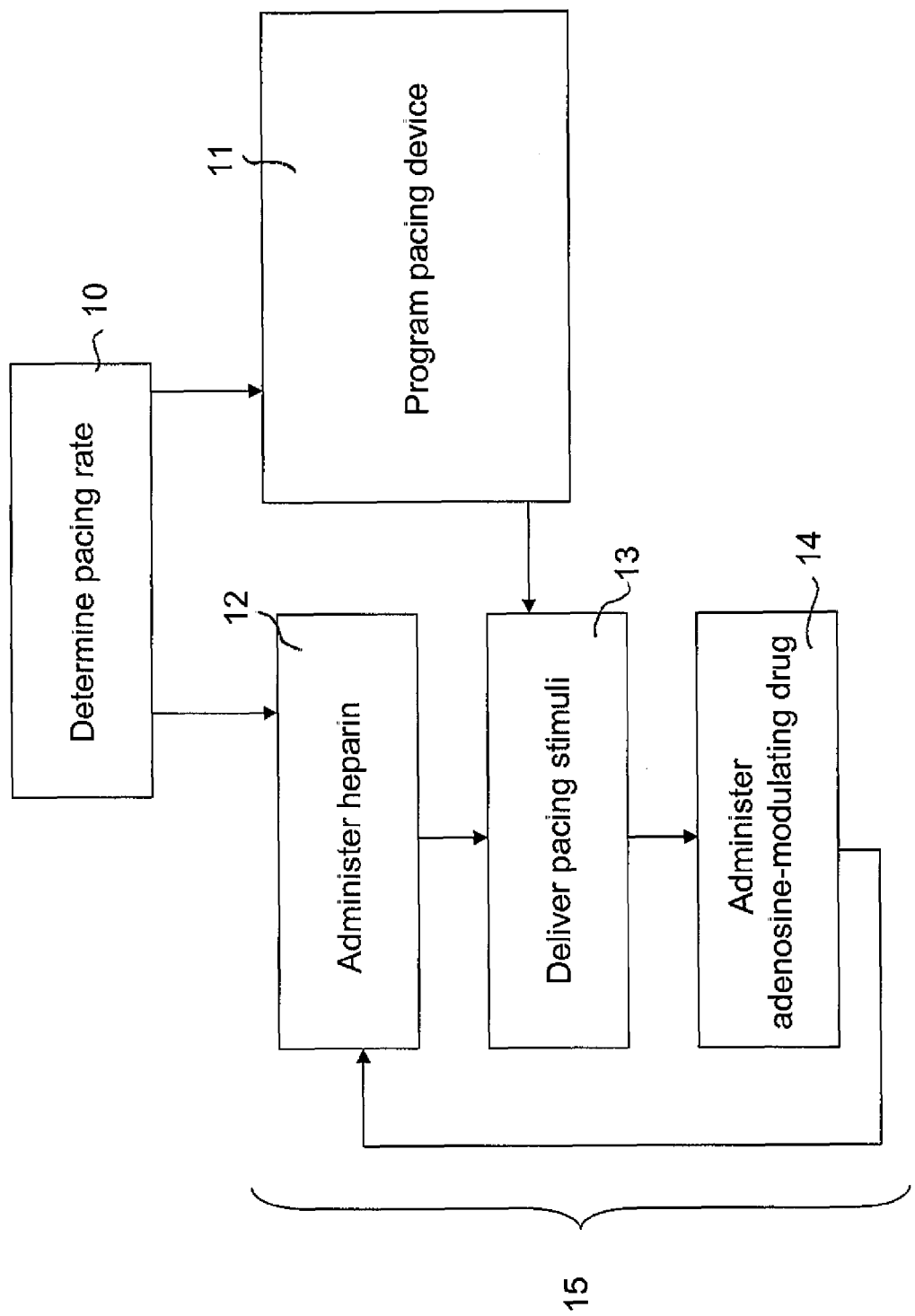
FIG. 1 is a flow chart outlining some methods of the present invention.

FIG. 1 is a flow chart outlining some methods of the present invention, which include a cycle 15 defined by a biochemical stimulus, followed by mechanical and metabolic stimulus, followed by another biochemical stimulus. According to FIG. 1, a first step 10 is to determine the pacing rate suitable to produce the mechanical and metabolic stimuli for a particular patient; the pacing rate is one at the threshold necessary to provoke ischemia in the patient, and may be determined via pacing stress echocardiography, or sampling the patient's blood pH or oxygen saturation during stress testing. Once the pacing rate is determined, a device implanted in the patient, for example a previously implanted pacemaker device, is programmed, per step 11, to deliver the ischemia-inducing pacing, per step 13, at a predetermined time for a pre-determined period of time. According to certain methods of the present invention, the predetermined time at which the pacing stimuli are delivered is established to be between step 12, in which heparin is administered, and step 14, in which the adenosine-modulating drug is administered. The pacing stimuli may be ramped up, in ten-beat increments every thirty seconds, to the ischemia inducing rate. According to one method of the present invention, approximately 5,000 units of heparin are delivered, per step 12, approximately five minutes prior to the period of pacing stimuli, per step 13. The period of pacing stimuli lasts between approximately five minutes and approximately thirty minutes, and then, approximately 10 milligrams of dipyridamole are delivered, per step 14, approximately one minute after the period of pacing stimuli. Preferably, cycle 15 is repeated twice a day for between approximately ten and approximately fifteen days, after which the patient may be tested, for example, via pacing stress echo or angiography, to determine the degree of collateral development attained by the method. If angiographic evaluation is pursued, a Rentrop score (ranging from 0=absent to 3=excellent) can be assigned to describe the degree of collateralization. Of course, the rate at which cycle 15 is applied and the number of days over which cycle 15 is repeated may be tailored to each individual patient's needs.

According to some embodiments of the present invention, the pharmacological agents of steps 12 and 14 are administered in a clinic or hospital intravenously, from a source external to the patient, and the patient's implanted device is programmed, for example, by an external programmer, via telemetry, just prior to starting cycle 15, or simultaneous with cycle 15, being controlled by a clinician operating the programmer during cycle 15. According to certain embodiments of the present invention, an implantable system includes the capability to deliver both the pacing stimuli and the agents providing the biochemical stimuli, and may be pre-programmed to carry out cycle 15 at a predetermined rate for a predetermined period of time. An example of such an implantable system is described in conjunction with FIGS. 2A-B and 3.

Figure 2A:
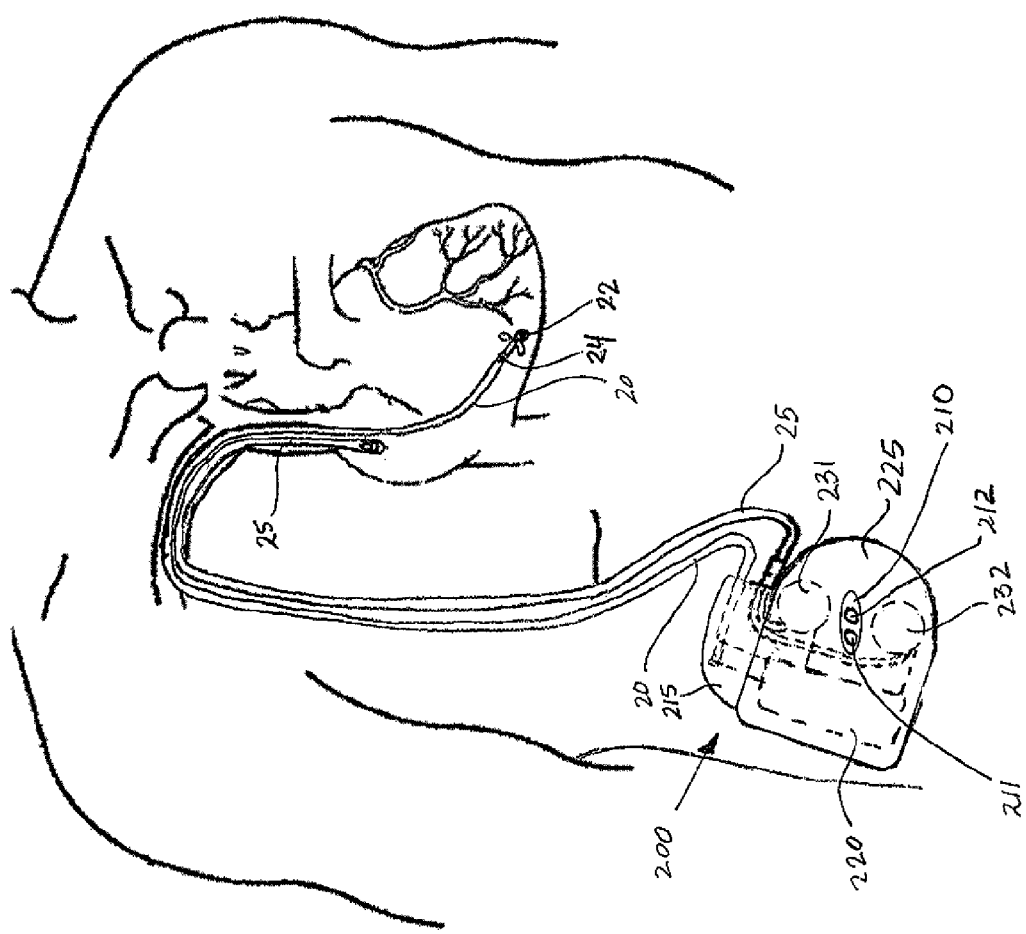
FIG. 2A is a schematic of an exemplary implanted system, according to some embodiments of the present invention.

FIG. 2A is a schematic of an exemplary implanted system, according to some embodiments of the present invention. FIG. 2A illustrates the system including a device 200 to which an implantable pacing lead 20 and an implantable fluid delivery tube or catheter 25 are coupled. Device 200 includes a housing or can 225 containing a first fluid pump 231, a second fluid pump 232, and pacing and pump electronic circuitry 220, for example, as represented in the block diagram of FIG. 3. Pacing lead 20 is shown including a pair of pace/sense electrodes 22 and 24 that are implanted in the right ventricle. A distal end opening of delivery tube 25 is shown disposed in the right atrium, but, may, alternately, be placed in the superior vena cava or another vessel of the venous system.

FIG. 2A further illustrates device 200 including a connector module 215 facilitating the coupling of device 200 with delivery tube 25 and lead 20; a first port of module 215 couples tube 25 to a pair of sealed passageways extending through a sidewall of housing 225, one connected to each of pumps 231 and 232, and a second port of module 215 includes a pair of electrical contacts, for electrical coupling of electronic circuitry 220 to pace/sense electrodes 22, 24 of lead 20. Those skilled in the art will appreciate that the pair of electrical contacts within the second port are coupled, via hermetically sealed electrical feedthroughs extending through the sidewall of housing 225, to electronic circuitry 220, and that lead 20 includes a pair of elongate insulated conductors extending from electrode pair 22/24 to a pair of connectors disposed on a proximal end of lead, which are inserted within the port for electrical connection with the contacts. Means for making and programming implantable medical devices to deliver pacing therapy are well known to those skilled in the art, as are means for making and programming implantable pumps to deliver therapeutic agents.

Figure 2B:
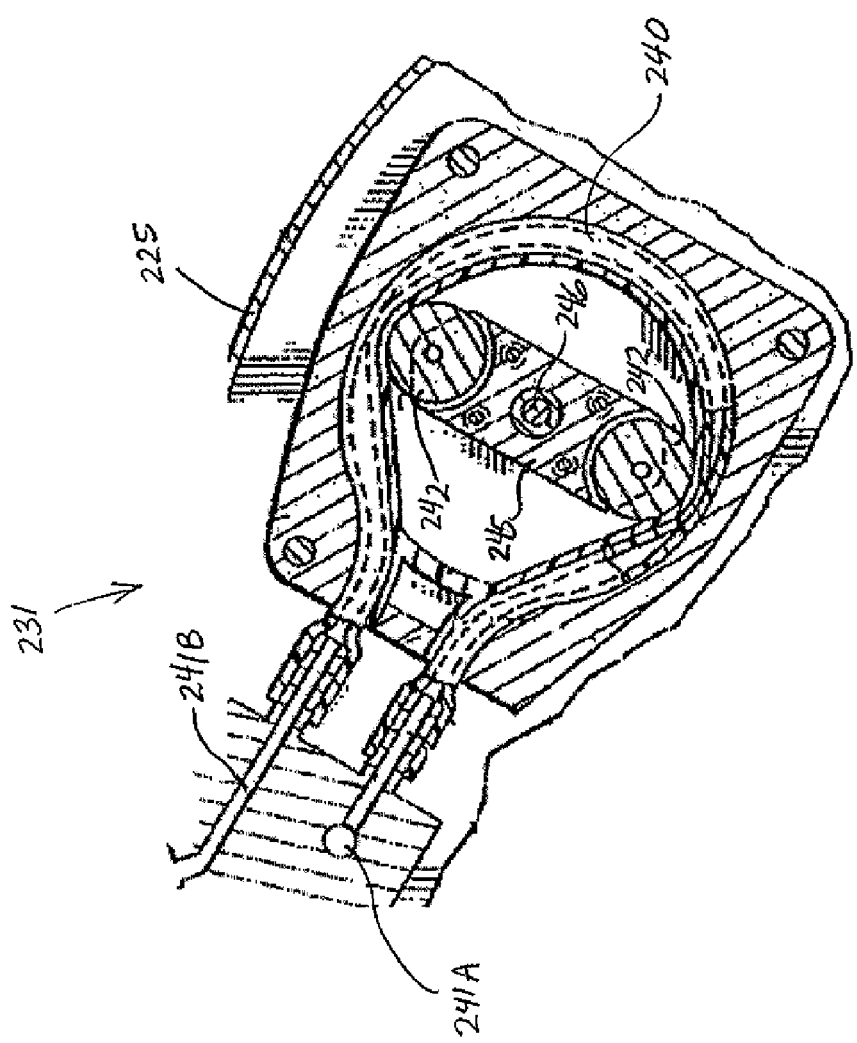
FIG. 2B is a section view through a portion of the system shown in FIG. 2A.

According to the exemplary embodiment of FIG. 2A, device 200 includes two roller or peristaltic pumps, such as those that are known to those skilled in the art; pump 231 includes a reservoir containing one of the heparin or adenosine-modulating drug and pump 232 includes a reservoir containing the other. Suitable components and construction methods that may be used to manufacture pumps 231 and 232 are found in commonly assigned U.S. Pat. No. 4,692,147, salient parts of which are hereby incorporated by reference. FIG. 2B is a section view through a portion of device 200 showing pump 231, which is similar to pump 232. FIG. 2B illustrates pump 231 including a flexible tube 240 extending from an inlet port 241A, which is coupled to a first fluid reservoir disposed behind pump 231, to an outlet port 241B, which couples to one of the pair of sealed passageways that is in fluid communication with tube 25; according to the illustrated embodiment, a shaft 246 rotates an arm 245 to which a pair of rollers 242 are attached. A bellows associated with a gas-filled pressure chamber (not shown) applies constant pressure against the reservoir, behind pump 231, to keep a volume of fluid in tube 240; when shaft 246 is energized, rollers 242 compress tube 240 to force a bolus of fluid out through port 241B and through delivery tube 25.

Referring back to FIG. 2A, device 200 further includes a fill port 210 mounted in a sidewall of housing 225; fill port 210 includes a first pierceable septum 211 providing access to the reservoir of pump 231 and a second pierceable septum 212 providing access to the reservoir of pump 232. Device 200 is implanted such that port 210 is disposed facing outward, toward the skin of the patient, so that each septum 211, 212 may be accessed via a transcutaneous needle stick to re-fill the reservoirs. Each pump reservoir may have a capacity to hold a volume of pharmacological agent sufficient for a number of cycles 15 (FIG. 1); when a patient visits a clinic or hospital for evaluation testing, the reservoirs may be transcutaneously re-filled, via ports 11, 12, for another round of therapy.

Figure 3:
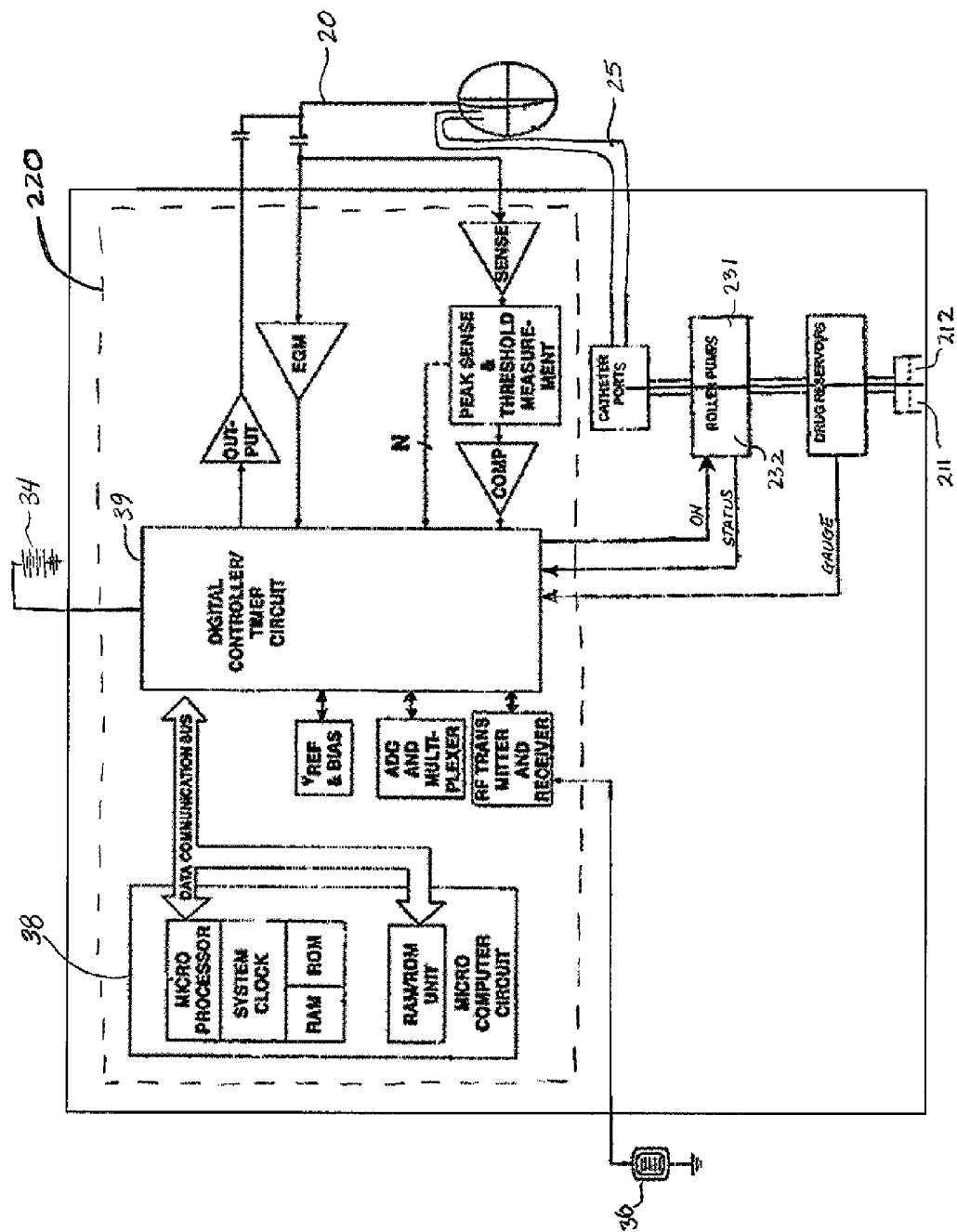
FIG. 3 is a block diagram of an exemplary system architecture, which may be employed by some embodiments of the present invention, for example, as illustrated in FIG. 2A.

FIG. 3 is a block diagram of an exemplary microprocessor-controlled system architecture, known to those skilled in the art and which may be employed by some embodiments of the present invention, for example, as illustrated in FIG. 2A. Furthermore, FIG. 3 illustrates a data communication bus extending between a microcomputer unit 38 and a digital timer/controller unit 39 to transfer, for execution, program instructions programmed in software of microcomputer unit 38 to unit 39. According to embodiments of the present invention, the instructions include commands to deliver angiogenic therapy, via pumps 231, 232 and pacing lead 20, for example, according to cycle 15 repeated at predetermined times, over a period of time, as previously described in conjunction with FIG. 1. FIG. 3 further illustrates a power source 34 for the electronic components and an RF transmitter and receiver coupled to an antenna 36 for communication with a device programmer. Although FIGS. 2A-B and 3 describe a system wherein a single device (200) includes pacing and pumping capacity, alternate system embodiments of the present invention include two independent devices, one delivering the pacing therapy and the other delivering the pharmacological agents. Each device, according to these alternate embodiments, may be independently programmed to function in synchrony with one another; or, one of the devices, or an external programmer, may include a microcomputer unit, for example, unit 38, from which the program instructions for angiogenic therapy, as described herein, are delivered to a timer/control unit, for example, unit 39, of each device.

In the foregoing detailed description, the invention has been described with reference to specific embodiments. However, it may be appreciated that various modifications and changes can be made without departing from the scope of the invention as set forth in the appended claims.

The invention claimed is:

1. A medical system configured to promote coronary angiogenesis in a patient, the system comprising:
   an implantable medical electrical pacing lead including at least one electrode, the at least one electrode being adapted to deliver cardiac pacing stimuli, when the pacing lead is implanted in the patient;
   a first fluid reservoir and a plurality of boluses of heparin, the first fluid reservoir containing the plurality of boluses of heparin;
   a first pump being coupled to the first fluid reservoir and being adapted to pump each bolus of heparin from the first reservoir;
   a second fluid reservoir and a plurality of boluses of an adenosine-modulating drug, the second fluid reservoir containing the plurality of boluses of the adenosine-modulating drug;
   a second pump being coupled to the second fluid reservoir and being adapted to pump each bolus of the adenosine-modulating drug from the second reservoir;
   a delivery tube coupled to the first reservoir and to the second reservoir, the delivery tube being adapted to deliver the boluses of the heparin and the adenosine-modulating drug into a venous system of the patient; and
   a microcomputer unit coupled to the pacing lead and to each of the first and second pumps, the microcomputer unit being programmed with instructions to control the lead and the pumps in order to execute a method for delivering angiogenic therapy according to the following steps:
      delivering a bolus of heparin through the delivery tube and into the venous system of the patient, the bolus of heparin being pumped, by the first pump, from the plurality of boluses of heparin contained in the first fluid reservoir;
      delivering the cardiac pacing stimuli via the at least one electrode of the implanted pacing lead for a predetermined period of time and at a rate that generally provokes myocardial ischemia in the patient, after delivering of the bolus of heparin; and
      delivering a bolus of the adenosine-modulating drug through the implanted delivery tube, and into the venous system of the patient, after delivering the pacing stimuli, the bolus of the adenosine-modulating drug being pumped, by the second pump, from the plurality of boluses of the adenosine-modulating drug contained in the second fluid reservoir.

2. The system of claim 1, further comprising:
   an implantable housing including a sidewall and containing the first and second pumps, the first and second fluid reservoirs, and the microcomputer unit;
   at least one feedthrough, extending through the housing sidewall, for electrical coupling of the lead to the microcomputer unit; and
   at least one passageway, extending through the housing sidewall, for coupling the delivery tube to the pump.

3. The system of claim 2, further comprising a fill port mounted in the housing sidewall and coupled to each of the first and second fluid reservoirs, the fill port being accessible transcutaneously.

4. The system of claim 1, wherein the delivery tube is implantable.

5. The system of claim 1, wherein:
   the delivered bolus of heparin is approximately 5,000 units; and
   the microcomputer unit is programmed to control the lead and the pumps so that the bolus of heparin is delivered approximately five minutes prior to delivering the predetermined period of the pacing stimuli.

6. The system of claim 1, wherein:
   the adenosine-modulating drug is dipyridamole and the delivered bolus of dipyridamole is approximately 10 milligrams; and
   the microcomputer unit is programmed to control the lead and the pumps so that the bolus of dipyridamole is delivered approximately one minute after delivering the pacing stimuli for the predetermined period of time.

7. The system of claim 1, wherein the predetermined period of time for delivery of the pacing stimuli is between approximately 5 minutes and approximately 30 minutes.

8. The system of claim 1, wherein the microcomputer unit is programmed to control the lead and the pumps so that the sequence of steps of delivering the bolus of heparin, delivering the pacing stimuli and delivering the bolus of adenosine-modulating drug are repeated twice a day.

9. The system of claim 1, wherein the microcomputer unit is programmed to control the lead and the pumps so that the sequence of steps of delivering the bolus of heparin, delivering the pacing stimuli and delivering the bolus of adenosine-modulating drug are repeated at least once a day for between approximately ten and approximately fifteen days.

\* \* \* \* \*